United States Patent [19]

Kinoshita

[11] 4,437,058
[45] Mar. 13, 1984

[54] INDICATING MEANS FOR MEASURING INSTRUMENT

[75] Inventor: Dainichiro Kinoshita, Kyoto, Japan
[73] Assignee: Horiba, Ltd., Kyoto, Japan
[21] Appl. No.: 274,368
[22] Filed: Jun. 17, 1981
[30] Foreign Application Priority Data
  Jul. 5, 1980 [JP] Japan .................................. 55-91988
[51] Int. Cl.³ ....................... G01R 19/26; G01N 27/42
[52] U.S. Cl. ..................................... 324/120; 324/438
[58] Field of Search ................. 324/120, 123 R, 99 D, 324/438

[56] References Cited
U.S. PATENT DOCUMENTS
2,710,397  6/1955  Foster ............................... 324/99 D
3,064,193  11/1962  Grubb et al. ..................... 324/123 R

*Primary Examiner*—Ernest F. Karlsen
*Attorney, Agent, or Firm*—Wenderoth, Lind & Ponack

[57] ABSTRACT

An indicating device for measuring instruments having a voltage-frequency converter for converting measurement signals expressed as voltage values into frequency signals with a frequency proportional to the voltage values, a counter for counting the frequencies of the frequency signals sent from the voltage-frequency converter and sending the counted number to an indicator for digitally indicating the measured values corresponding to the counted number. A switch is connected between the voltage-frequency converter and the counter, and a controller for holding the switch in the closed state only during a predetermined time is connected to the switch. Analog signals sent from the measuring device can be indicated digitally and the digital values indicated can be held by a simple, inexpensive and miniaturizable construction.

6 Claims, 2 Drawing Figures

INDICATING MEANS FOR MEASURING INSTRUMENT

FIELD OF THE INVENTION

The present invention relates to an indicating means for measuring instruments.

BACKGROUND OF THE INVENTION AND PRIOR ART

The conventional A/D converter, which has been used for indicating in digital form analog signals obtained by measurements, has chiefly carried out a continuous A/D conversion. Thus it is necessary to provide a separate holding mechanism in order to hold the values of the signals in digital form and the electric circuit is made complicated, and apparatus becomes expensive. Furthermore, such a conventional A/D convertor is large-sized and has not been miniaturized because of the shape, specification, power supply and the like of an A/D converting element thereof.

OBJECT AND BRIEF SUMMARY OF THE INVENTION

It is an object of the present invention to provide an indicating means for measuring instruments which can indicate in digital form analog signals sent from the analytical portion of the instrument and hold said signals in digital form by a simple, inexpensive and miniaturizable construction, so that the above described deficiencies of the prior art converters are overcome.

This object is achieved by providing an indicating means for measuring instruments producing measurement signals expressed as voltage values, said indicating means comprising a voltage-frequency converter for converting the voltage signals into frequency signals with a frequency proportional to the value of the voltage signals, frequency sensing means connected to said voltage frequency converter for sensing the frequency of the frequency signals, an indicator connected to said frequency sensing means for receiving the sensed frequency and for digitally indicating the sensed frequency as a value corresponding to the measured value, a switch connected between said voltage-frequency converter and said frequency sensing means, and a controlling means connected to said switch for holding said switch in a closed state for a predetermined time for enabling said frequency sensing means to sense the frequency of the frequency signals.

BRIEF DESCRIPTION OF THE DRAWINGS

The invention will be described in greater detail in connection with the accompanying drawings, in which.

DESCRIPTION OF THE PREFERRED EMBODIMENT

Figure 1:
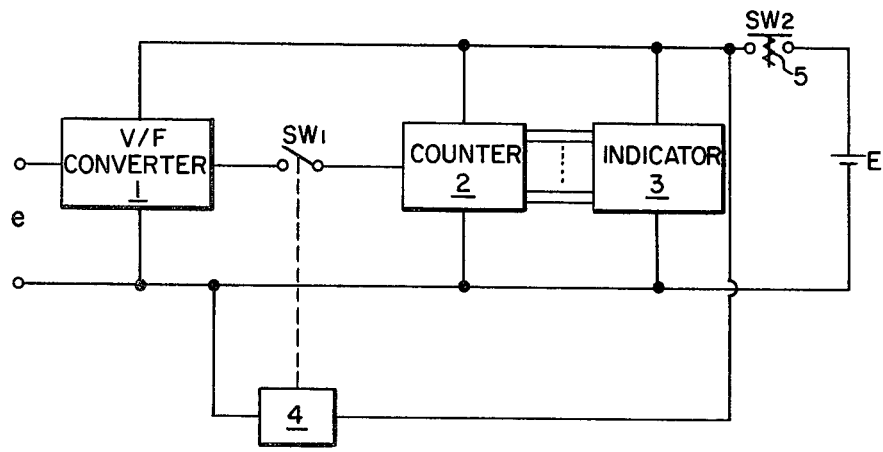
FIG. 1 is a diagram of an electric circuit of an indicating means according to the present invention.
Figure 2:
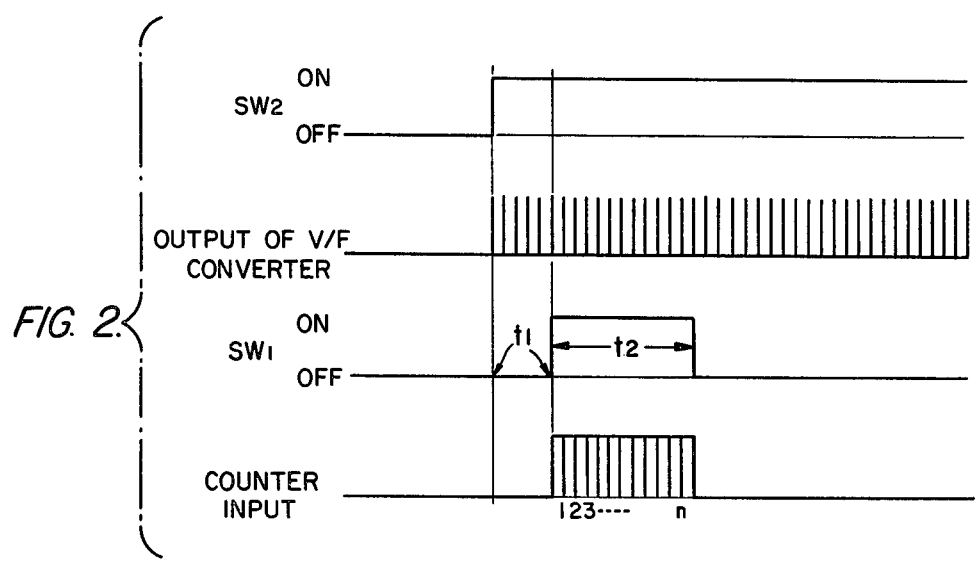
FIG. 2 is a diagram showing the action of the main portion of an indicating means according to the present invention.

As seen in FIG. 1, the electric circuit of an indicating means according to the present invention is comprised of a voltage-frequency converter 1 (referred to as a V/F converter hereinafter) for converting voltage signals corresponding to the measured values, e.g. an impedance-converted differential voltage between a comparison electrode and a glass electrode corresponding to a value of pH, expressed by a value of voltage e, into a signal, the frequency of which is in direct proportion to the value of the voltage. A frequency sensor, here shown as a counter 2 including a driver, is connected to the V/F converter as a means for sensing the frequency of the signal from said V/F converter 1, for example by counting the pulses thereof, and sending the sensed value, e.g. the counted number n, to an indicator 3 for digitally indicating the measured value, such as the value of pH, for example pH=2.0 corresponding to said sensed frequency, e.g. the counted number n sent from said counter 2. A $SW_1$ is connected between said V/F converter 1 and said counter 2. A power supply E is connected across the indicator 3, and a main switch $SW_2$ is connected in said power supply circuit. A controlling means 4 is connected to switch $SW_2$ for holding said switch $SW_1$ in the closed state only during a predetermined desired period of time $t_2$ after the passage of a predetermined period of time $t_1$, as shown FIG. 2. Controlling means 4 is operated when said switch $SW_2$ is closed against the action of a spring 5. The controlling means can be, for example, a one-shot circuit.

Consequently, closing said main switch $SW_2$ by actuating it by a finger causes said switch $SW_1$ to be held in the closed state only during the period of time $t_2$ after passage of the time $t_1$, and thereby the output of said V/F converter 1 is sent to said counter 2, the frequency is determined, e.g. by counting the pulses for time $t_2$, and the value, e.g. the counted number of pulses n during the time $t_2$, is sent to said indicator 3 which digitally indicates the measured value (for example pH=2.0) coorresponding to the number n of pulses counted only during said period of time $t_2$. After passage of time $t_2$, the switch $SW_1$ is opened for time $t_1$ and then closed again for time $t_2$. Then, when the finger is removed from said main switch $SW_2$, said main switch $SW_2$ is opened by the action of said spring 5 to stop the digital indications from said indicator 3.

Said predetermined time $t_1$ is the time for stabilizing the electric circuit after a counting operation, and accordingly said predetermined time $t_1$ is not required when said electric circuit is instantly stabilized.

The indicating means according to the present invention having the above-described construction eliminates a need for the conventional A/D converter element and a supplementary holding mechanism and thereby the construction thereof has been simplified as compared with the prior art device. Thus an indicating means according to the present invention can be made inexpensively and can be miniaturized. In addition, according to the present invention, it is necessary only to electrically charge the indicator 3 in order to read the digital values of the measurements being supplied continuously. This is a great practical advantage.

It will be of course be understood that the indicating means according to the present invention may be used for measuring instruments other than pH meters, the indicating means being described above for a pH meter being only the preferred embodiment of the invention.

What is claimed is:

1. An indicating means for measuring instruments producing measurement signals expressed as voltage values, said indicating means comprising a voltage-frequency converter for converting the voltage signals into frequency signals with a frequency proportional to the value of the voltage signals, frequency sensing means connected to said voltage frequency converter for sensing the frequency signals, an indicator connected to said frequency sensing means for receiving the sensed frequency and for digitally indicating the sensed frequency as a value corresponding to the measured value, a first switch connected between said voltage-frequency converter and said frequency sensing means, a power source, connected to at least one of said voltage-frequency converter, said frequency sensing means and said indicator, a second switch connected between said power source and said at least one of said voltage-frequency converter, said frequency sensing means and said indicator, for providing operating power from said power source to said at least one of said voltage-frequency converter, said sensing means and said indicator only when said second switch is closed, and a controlling means connected to said first switch, responsive to closing of said second switch, for holding said first switch in an open state for a first predetermined time for permitting said frequency sensing means to stabilize, and in a closed state for a second predetermined time following said first predetermined time, for enabling said frequency sensing means to sense the frequency of the frequency signals during said second predetermined time.

2. An indicating means as claimed in claim 1 in which said voltage-frequency converter provides a pulsed frequency signal and said frequency sensing means is a counting means for counting the pulses in said predetermined time.

3. An indicating means as claimed in claim 2 in which said counting means is a counter having a driver.

4. An indicating means as in claim 1, wherein said at least one of said voltage-frequency converter, said frequency sensing means and said indicator comprises each of said voltage-frequency means, said frequency sensing means, and said indicator.

5. An indicating means for a pH meter producing measurement signals of measured values of pH as voltage values, said indicating means comprising a voltage-frequency converter for converting the voltage signals into frequency signals with a frequency proportional to the value of the voltage signals, frequency sensing means connected to said voltage frequency converter for sensing the frequency of the frequency signals, an indicator connected to said frequency sensing means for receiving the sensed frequency and for digitally indicating the sensed frequency as a value corresponding to the measured value, a first switch connected between said voltage-frequency converter and said frequency sensing means, a power source, connected to at least one of said voltage-frequency converter, said frequency sensing means and said indicator, a second switch connected between said power source and said at least one of said voltage-frequency converter, said frequency sensing means and said indicator, for providing operating power from said power source to said at least one of said voltage-frequency converter, said frequency sensing means and said indicator only when said second switch is closed, and a controlling means connected to said first switch, responsive to closing of said second switch, for holding said first switch in an open state for a first predetermined time for permitting said frequency sensing means to stabilize, and in a closed state for a second predetermined time following said first predetermined time, for enabling said frequency sensing means to sense the frequency of the frequency signals during said second predetermined time.

6. An indicating means as in claim 5, wherein said at least one of said voltage-frequency converter, said frequency sensing means and said indicator comprises each of said voltage-frequency means, said frequency sensing means, and said indicator.

* * * * *